United States Patent [19]

Hopkins

[11] Patent Number: 4,458,681
[45] Date of Patent: Jul. 10, 1984

[54] STOMACH CLAMP FOR AND METHOD OF PROXIMAL GASTRIC PARTITIONING

[76] Inventor: Donald A. Hopkins, 4905 Harrison Cir., Gulfport, Miss. 39501

[21] Appl. No.: 387,078

[22] Filed: Jun. 10, 1982

[51] Int. Cl.³ .............................................. A61B 17/08
[52] U.S. Cl. .................................................. 128/346
[58] Field of Search .......... 128/303 R, 334 R, 334 C, 128/346, 1 R; 285/419; 138/99

[56] References Cited

U.S. PATENT DOCUMENTS

| 2,123,414 | 7/1938 | Gilmore | 138/99 X |
| 2,659,371 | 11/1953 | Schnee | 128/346 |
| 2,842,122 | 7/1958 | Butler | 604/408 X |
| 4,246,893 | 1/1981 | Berson | 128/1 R |

FOREIGN PATENT DOCUMENTS 120667 11/1918 United Kingdom .................. 138/99

OTHER PUBLICATIONS

V. Mueller & Co., Catalogue, 1963, pp. 144, 128-346.

Primary Examiner—Dalton L. Truluck
Attorney, Agent, or Firm—James B. Lake, Jr.

[57] ABSTRACT

A stomach clamp, having partially occluding arms that extend across a stomach, is operationally clamped in place by bolting together opposed arm ends that extend beyond the stomach periphery. The clamp divides the stomach and reduces space for food input while permitting drainage between the divided stomach parts through the non-occluding part of the clamp arms. The clamp is semi-permanently installed without penetration of stomach lumen or gastrointestinal tract and serves to reduce food intake ane obesity. Frictional engagement of the arms with the stomach is reinforced with sutures through outer layers of the stomach.

2 Claims, 9 Drawing Figures

STOMACH CLAMP FOR AND METHOD OF PROXIMAL GASTRIC PARTITIONING

BACKGROUND OF THE INVENTION

The invention relates generally to adjustable clamping devices, and more particularly to a stomach clamp for and method of proximal gastric partitioning.

No stomach clamps were found in a preliminary search of the prior art, but U.S. Pat. Nos. to Artandi et al 3,272,204; Pease, Jr. 2,671,444; Jimenez 3,266,054; Usher 3,124,136 and 3,054,406 were cited as showing materials that might be used in the construction of a stomach clamp. Two methods of proximal gastric partitioning are known, however; "gastric stapling" and "gastric bypass," both of which leave the stomach in altered anatomical configuration permanently.

The invention teaches new apparatus that is semi-permanent and easily installed without penetrating into stomach lumen or gastrointestinal tract, and easily removed to leave the stomach anatomically unaltered in a new method of gastric partitioning.

SUMMARY OF THE INVENTION

The invention limits the effective size of a stomach with an adjustable, atraumatic, partially occluding clamp that is placed across the stomach to partition it into a small upper or proximal stomach pouch and a lower or distal pouch, with the proximal pouch opening distally for satisfactory drainage into the distal pouch and gastrointestinal tract. The reduction of stomach effective size provides early satiety with less food intake and therefore serves as an anti-obesity means and method as does the prior art cited above. Less surgical dissection, less specialized instruments and less operating time results in less danger of infection and reduced costs.

It is an object of the invention to provide proximal gastric partitioning with no penetration of the stomach lumen and no invasion of the gastrointestinal tract.

A further object of the invention is to provide adequate drainage between the partitioned parts.

Yet another object of the invention is to provide proximal gastric partitioning that is semipermanent and easily removable to leave the stomach unaltered anatomically.

DETAILED DESCRIPTION OF THE PREFERRED EMBODIMENTS

Figure 1:
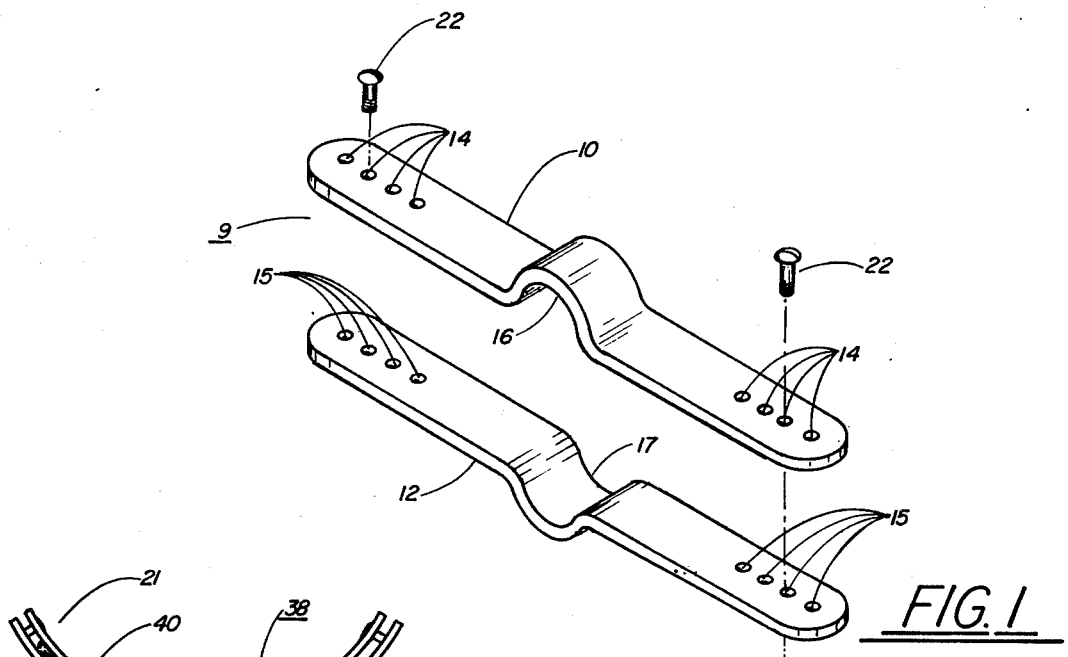
FIG. 1 is a three dimensional exploded view of a preferred embodiment of the invention.
Figure 2:
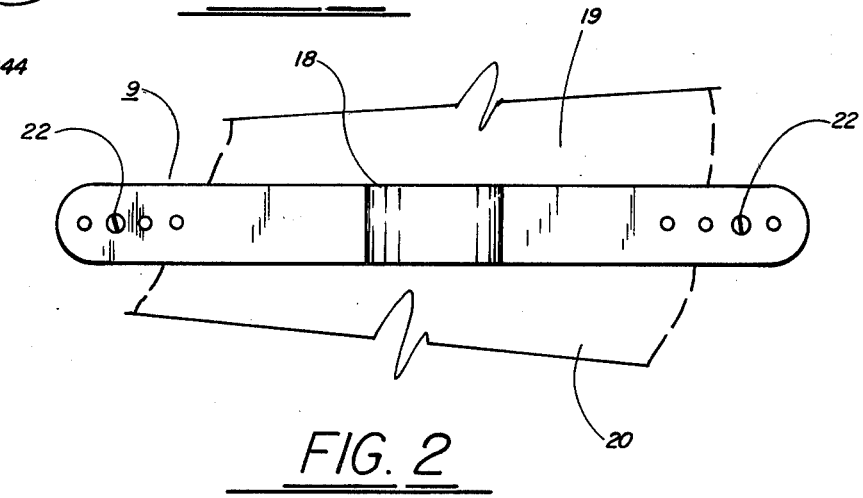
FIG. 2 is a plan view of the invention positioned across a section of stomach.
Figure 3:
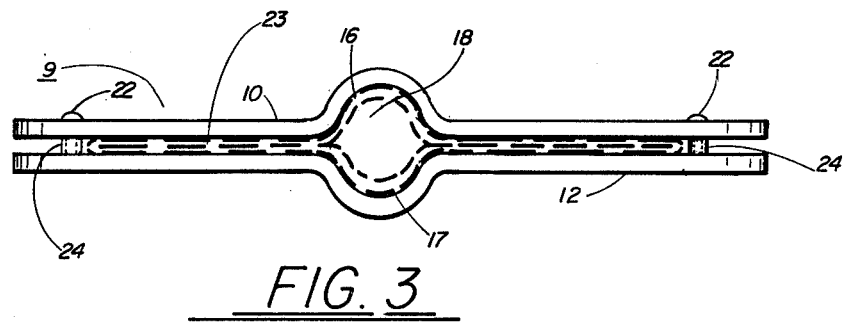
FIG. 3 is a side elevation of the matter of FIG. 2.

Referring to FIGS. 1-3, a preferred embodiment 9 of the invention comprises two longitudinally extending clamping arms 10 and 12 having defined in their respective ends a plurality of bolt holes 14 and 15 that are longitudinally spaced apart for opposing registration of the holes of one arm with those of the other arm. Each of the clamping arms 10 and 12 defines a transverse half-cylinder 16 and 17, respectively, and with each similarly intermediate the associated ends and end holes 14 and 15, of which holes 15 are threaded. Transverse half-cylindrical passages 16 and 17, with arms 10 and 12 and the passages 16 and 17 opposed, define a cylindrical drain 18 between the proximal and distal pouches 19 and 20 respectively defined above and below said clamping arms, when secured together at respective ends by threaded bolts 22 passing through holes 14 and engaging in registering threaded holes 15 beyond the outer periphery of stomach 23 (see FIGS. 2 and 3). Spacer sleeves 24, between arms 10 and 12 and around bolts 22, prevents overpressurizing the stomach areas under said arms. Multiple sutures (not shown) reinforce frictional engagement of the arms to hold the arms in place. The sutures penetrate only the outer layers of the stomach and are removable, leaving the stomach lumen intact.

Figures 5, 8:
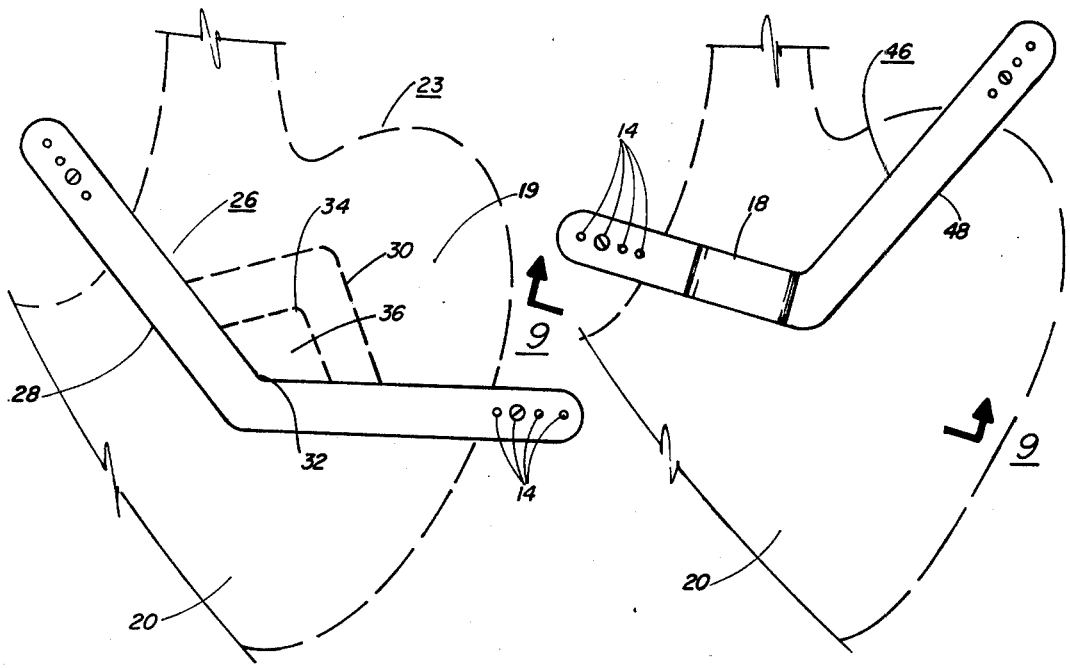
FIG. 5 is a plan view of a second embodiment of the invention positioned for proximal gastric partitioning.
FIG. 8 is similar to FIG. 5, but of a second version of the second embodiment.
Figure 6:
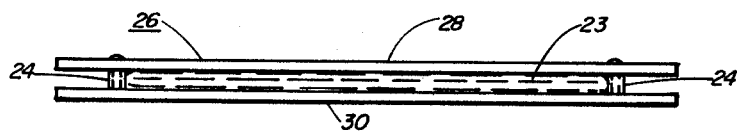
FIG. 6 is a side elevation of the matter of FIG. 5.
Figure 7:
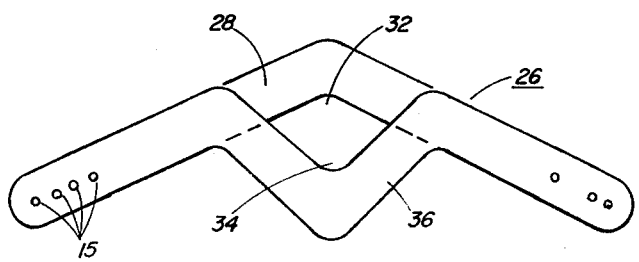
FIG. 7 is a bottom view of the clamp of FIG. 5.

Referring to FIGS. 5-7, a second embodiment 26 comprises elongated angular clamping arms 28 and 30 wherein opposed but non-conforming angles 32 and 34 are defined between the ends of said clamping arms that define holes 14 and 15 as in embodiment 9. Nonconforming angles 32 and 34 leave an unclamped area between clamping arms 28 and 30 that constitutes a drain 36 between the proximal and distal pounches 19 and 20 of stomach 23 above and below said angular clamping arms.

Figure 4:
FIG. 4 is similar to FIG. 3 but of a second version of the preferred embodiment.

Referring to FIGS. 4, a second version 38 of the preferred embodiment comprises longitudinally curved clamping arms 40 and 42 with an off center drain 44 defined between said arms. The curved clamping arms act in the same way as clamping arms 10 and 12, but in a few cases are easier to apply.

Figure 9:
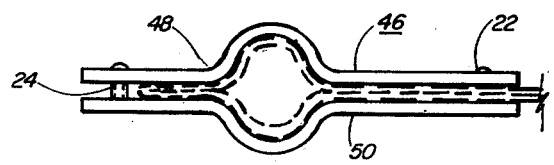
FIG. 9 is a side elevation similar to FIG. 6 but of the second version of the second embodiment of the invention.

Referring to FIGS. 8 and 9, a second version 46 of the second embodiment 26 comprises comprises angular clamping arms 48 and 50 that have similar conforming angles 52, and transverse half cylindrical passages defining a cylindrical drain similar to drain 18 of the preferred embodiment 9, and as shown in FIG. 8.

In the operation of both embodiments and versions described, the respective clamping arms of the invention are opposed across the respective sides of a of a stomach, and a bolt for the clamping arms' ends engaged in registering holes between which no stomach portion intervenes. The loosely connected clamping arms are adjusted across the stomach as shown in FIGS. 5 or 8, and the bolts tightened as limited by space sleeves 24 to prevent overpressurizing stomach areas between the respective arms. The sides of the stomach are pressed together, except for the transverse drain defined between said clamping arms, to partition the stomach into proximal and distal pouches without puncturing the stomach lumen and without cutting into the gastrointestinal tract. The reduced proximal part of the stomach decreases the amount of food that can be received into the stomach for early satiety and less calorie intake.

Clamp installation is semi-permanent, and the clamp can be easily removed surgically if needed, and will leave the stomach and gastrointestinal tract anatomically unimpaired.

What is claimed is:

1. A stomach clamp for proximal gastric partitioning comprising:
   (a) a pair of elongated clamping arms, having opposite and non-conforming parts, for positioning in generally parallel opposition to define a partially occluding clamp with oppositely disposed ends extending transversely beyond and across any stomach;
   (b) fastening means for adjustably fastening together the oppositely disposed ends of the respective clamping arms, said fastening means being a plurality of equally sized and spaced holes transversely defined in the oppositely disposed ends of said respective clamping arms for sets of end pairs of said holes to register just beyond the limits of any size stomach, when said clamping arms are parallelly opposed, said holes of one of the clamping arms being threaded, and a pair of bolt means, one for each registering pair of holes at each clamp end, for passing through the unthreaded holes and engaging in the threaded holes;
   (c) transverse passage means defined between said opposed clamping arms in combination by said opposite and non-conforming parts intermediate the respective oppositely disposed clamped arm ends for making said clamp partially occuded; and
   d. spacing means mounted between said oppositely disposed ends of the respective clamping arms for making the clamp atraumatic in application.

2. Method of proximal gastric partitioning comprising the steps of:
   (a) placing the arms of a two piece adjustable clamp across a stomach between the proximal and distil opening thereof;
   (b) tightening the joined ends of said clamp arms to partition said stomach into proximal and distal pouches, respectively above and below said clamp;
   (c) defining a transverse drain between said clamp arms and said proximal and distal pouches with non-occluding clamp arms' parts,
   (d) retaining said clamp in place by a combination of frictional engagement between clamp and stomach, and sutures through outer layers of said stomach without puncturing the stomach lumen.

* * * * *